United States Patent [19]

Leveen et al.

[11] Patent Number: 5,110,801
[45] Date of Patent: May 5, 1992

[54] TREATMENT OF ACNE

[76] Inventors: Harry H. Leveen, 321 Confederate Cir., Chlarleston, S.C. 29407; Robert F. Leveen, 312 Lambard St., Philadelphia, Pa. 19147

[21] Appl. No.: 313,481

[22] Filed: Feb. 22, 1989

Related U.S. Application Data

[63] Continuation-in-part of Ser. No. 80,995, Aug. 3, 1987, abandoned, which is a continuation of Ser. No. 640,190, Aug. 13, 1984, Pat. No. 4,684,627.

[51] Int. Cl.$^5$ .................. A61K 31/70; A61K 31/045; A61K 31/12; A61K 31/19
[52] U.S. Cl. .................................. 514/34; 514/25; 514/53; 514/557; 514/689; 514/733; 514/859; 514/864
[58] Field of Search ............... 514/733, 859, 864, 689, 514/734, 25, 421, 23, 62, 553, 557, 34, 53

[56] References Cited

U.S. PATENT DOCUMENTS

| | | | |
|---|---|---|---|
| 3,006,810 | 10/1961 | Shinn et al. | 514/733 |
| 3,006,811 | 10/1961 | Shinn et al. | 514/733 |
| 3,085,933 | 4/1963 | Schooley et al. | 514/733 |
| 3,272,702 | 9/1966 | Schooley et al. | 514/733 |
| 3,523,937 | 8/1970 | Biegeleisen | 536/17.4 |
| 4,272,508 | 6/1981 | Tamm | 514/178 |
| 4,326,055 | 4/1982 | Loeligek | 514/859 |
| 4,367,227 | 1/1983 | Bingham | 514/859 |
| 4,456,620 | 6/1984 | Laurent et al. | 514/859 |
| 4,473,551 | 9/1984 | Schinitsky | 514/21 |
| 4,507,287 | 3/1985 | Dixon | 514/859 |
| 4,565,806 | 1/1986 | Setala | 514/54 |
| 4,565,863 | 1/1986 | Bollag et al. | 536/18.2 |
| 4,588,750 | 5/1986 | Boris | 514/765 |
| 4,657,901 | 4/1987 | Ueda et al. | 514/171 |
| 4,684,627 | 8/1987 | Leveen et al. | 514/25 |
| 4,814,324 | 3/1989 | Borris et al. | 514/26 |

FOREIGN PATENT DOCUMENTS 0071165 2/1983 European Pat. Off.
0170269 2/1986 European Pat. Off.

OTHER PUBLICATIONS

Lazo et al.; Febs Letters 98 (1): 88–90, (Feb. 1979).
Arita, et al.; J. Biochem. 88 (5): 1399–1406 (1980).
Holstege et al.; Eur. J. Biochem. 121: 469–474 (1982).
The Merck Manual; 15th Ed.; Berkow et al., Eds. pp. 2277–2280 Publ. Merck, Sharp & Dohme Research Labs (1987).
Yamamura et al.; Chemical Abstracts 86:169357h (1977).
Noda Shokkin Kogyo; Chemical Abstracts 100:33273c (1984).
The Merck Manual; 15th Ed. pp. 2265–2266 (1987).
Shamberev et al.; Chemical Abstracts 71:120110y (1969).
Glass; Chemical Abstracts 93:210243c (1980).
Chemical Abstracts, vol. 67, 115099q, 1967, Evidence for Carrier-Mediated Transport of Monosaccharides in the Ehrlich Ascites Tumor Cell, Kolber et al.
Chemical Abstracts, vol. 73, 12924q. 1970, Effect of Glucose and ATP on the Respiration of Ascitic Cancerous Cells in the Presence of Phlorizin and Ouabain, Ilinich et al.
Dialog Information Service, Embase 74–79, 77012446, Kinetics of 2-Deoxy-D-Glucose Transport into Cultured Mouse Neuroblastoma Cells, Walum et al.
Dialog Information Service, Embase 80–81, 81246326, The Hexose Transport System in the Human K-562 Chronic Myelogenous Leukemia Derived Cell, Dozier et al.
Dialog Information Service, Data Base 72, Embase 82–88, 86187256, Decrease in Glucose Transport Activity of Friend Erythroleukemia Cell Caused by Dimethylsulfoxide, a Differentiation-Inducing Reagent, Kasahara et al.
Dialong Information Service, Data Base 72, Embase 82–88, 86199919, Effects of Insulin on Glucose Transporters and Metabolic Patterns in Harding-Passey Melanoma Cells, Delicado et al.

Primary Examiner—Johnnie R. Brown
Assistant Examiner—Nancy S. Carson
Attorney, Agent, or Firm—John S. Hale

[57] ABSTRACT

Acne is treated by administering to the subject a substance which is effective in blocking glucose entry into sebaceous cells, thereby inhibiting the production of sebum by these cells. Typically, the substance is administered topically and is dissolved or suspended in an appropriate solvent. The preferred substance is phloretin, which can for example, be dissolved in propylene glycol.

5 Claims, No Drawings

TREATMENT OF ACNE

RELATED CASES

This application is a continuation-in-part of U.S. patent application Ser. No. 080,995 filed Aug. 3, 1987, now abandoned, which is a continuation of U.S. patent application Ser. No. 640,170 filed Aug. 13, 1984, now U.S. Pat. No. 4,684,627.

BACKGROUND OF THE INVENTION

Acne is a skin disease with usual onset at adolescence. It is characterized by the overproduction of sebum. One principle in treating acne has been to reduce the secretion of sebum. At the time of puberty, the sebaceous glands responding to hormonal influences increase the production of sebum excessively. Prior to the present invention, sebum secretion could only be suppressed by estrogen administration which is satisfactory for the treatment of females, but the side effects contraindicate the use of systemic estrogen in males. Labeled studies indicate that sebaceous cells form sebum from glucose. Glycogen is first synthesized and is then converted to grease and extruded into the duct as sebum.

An understanding of the roll of glucose in the synthesis of sebum is important. Factors governing glucose entry into the sebaceous cell are similar to those found in other cells where insulin plays a prominent role. The utilization of glucose by the skin of diabetics is diminished, but is enhanced by insulin in both normals and diabetics. The pathways to the synthesis of fatty acid are enhanced by insulin. (Can.J.Biochem. 44:801 1966). The stimulating effect of insulin on acne vulgaris has been demonstrated, (Zeit of Haut & Geschects Krank. 41:429 1966) and this investigation proved that lipids were synthesized by the skin under the influence of insulin. Wheatly presented a simple method for testing the formation of lipids in thin tissue slices. His data indicated that C-14 labeled glucose was the best precursor for the synthesis of cutaneous lipids. (J.Clin. Invest. Derm. 54:288 1970). It has also been found that drugs that interfere with sterol synthesis do not influence sebum formation. (Brit. J. Derm. 81:280 1969).

The normal sebaceous gland contains immature cells at the periphery of the sebaceous acini. These cells contain large nuclei which are usually larger than the cytoplasm. As the peripheral cells mature, large quantities of glycogen accumulate in the cytoplasm. This accumulation of glycogen results from the entrance of glucose into the cell and its conversion to glycogen. This anabolism appears to be stimulated by androgens. As cells undergo sebaceous transformation glycogen decreases concomitantly with the increase of lipid globules. (J.Invest.Dermatol. 17:147 1951; Anat. Rec. 114:231 1952). The concentration of glycogen in the cell is inversely related to the lipid concentration since it is decreased by the conversion of glycogen to lipid. As the concentration of lipid increases, the entire cell becomes converted to a mass of lipid. The entire lipid rich cell is destroyed and extruded into the duct of the gland. New cells at the periphery grow and replace the extruded cell.

Phloridzin is a glucoside which is a natural plant hormone present in apple root bark (Merk Index 1983 10:7211) and the seeds of young apple fruit (Nature 158:663 1946). The aglucone portion of phloridzin is a phenolic compound called phloretin. (Merk Index 10:7210 1983). Phloretin is insoluble in water and soluble in acetone and alcohols and sparingly soluble in the fat solvents benzene and chloroform, but phlorizin is soluble in hot water and alcohol, but insoluble in chloroform and benzene. Both phloridzin and phloretin are known generally to prevent the entrance of glucose into cells by blocking the glucose transfer sites on the cell membrane (Physiol. Rev. 25:255 1945; Harvey Lect. 56:63 1961). These compounds therefore prevent glycogen formation in cells and lead to glycogen depletion. They are relatively non-toxic and have been systematically administered to humans and animals. (Physiol.-Rev. 7:385 1927) (Physiol.Rev. 25:255 1945; Am.J.-Physiol. 219:1080 1970). Animals and humans respond to systemic administration with glucosuria since these drugs prevent tubular reabsorbtion of glucose from the glomerular filtrate. (Smith, H.S. *The Kidney*, Oxfor Univ. Press 1951, p. 97). Although phloridzin and phloretin have been extensively studied, they have remained medical curiosities with no previously known medicinal use.

SUMMARY OF THE INVENTION

The present invention relates to a method for treating acne by administering compositions such as phloridzin, phloretin, and stilbesterol compounds which inhibit the production of sebum by denying the sebaceous cells the necessary building blocks for the synthesis of sebum.

DETAILED DESCRIPTION OF THE INVENTION

In accordance with the present invention, acne vulgaris is treated by suppressing the production of sebum in sebaceous cells by topically administering medications which block the glucose receptor sites on the surface of sebaceous cells to thus prevent glucose entry into the cell thereby preventing synthesis of glycogen or sebum. Various compositions have been found to be effective for use in the treatment of acne according to this invention, however, the preferred compositions are phloretin and its lipid soluble analogs as well as stilbesterol compounds.

Although both phloridzin and phloretin inhibit glucose entry into the cell by blocking the receptor site for glucose transfer, phloretin is preferred since it is lipid soluble. The skin is a perfect lipid barrier and water soluble compounds do not penetrate to the depths of the skin surface and cannot reach the surfaces of the sebaceous cells if topically applied. Only non polar compounds penetrate the skin. Therefore, a non polar solution of topical phloretin does inhibit glucose entry in the cell when applied to the skin. Phloretin has a structural formula as indicated below.

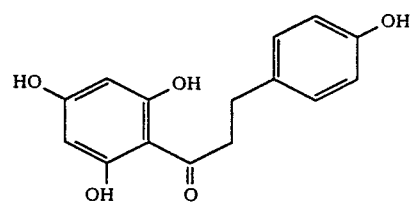

PHLORETIN

-continued

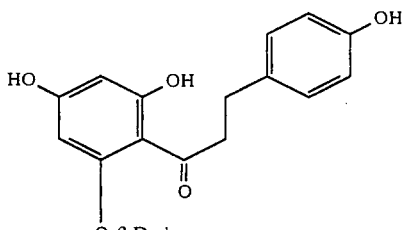

O-β-D-glucose

PHLORIDZIN

LeFerve who studied glucose transport in the red blood cell found that many other diphenolic compounds such as stilbesterol also inhibited sugar transport across the red cell membrane. He compared the various compounds to one another and rated phlorizin as having a potency of 1.9 while phloretin has a potency of 160 which was the same as stilbesterol. However, 3.3'-di(chlorallyl) stilbesterol had a potency of 1600 and 3-3' diallyl stilbesterol had a potency of 1000. (Phamacol. Rev. 13:39 1961) Phlorizin is more active than phloretin in blocking glucose transport by renal tubular epithelium and intestinal mucosa where glucose transport is dependent on sodium transport. (Biochemica et Biphysica Acta 288:145 1972; Am. J. Physiol 203:975 1963) Other cells act like red blood cells where phloretin is more active.

Since phloritin and diallyl stilbesterol are relatively non polar compounds they are effective topically when dissolved in suitable skin penetrants. It can be diluted to a 0.5 to 2 percent by weight solution in a solvent such as propylene glycol. A lesser concentration is required for the stilbesterol compounds. Upon inunction, they penetrate the skin and those glucose transfer sites on the surface of the skin are blocked. The sebaceous cells become impermeable to glucose for a prolonged period and sebum synthesis ceases. Since excessive sebum secretion is thought by some to be the cause of acne, and since the disease responds favorably to inhibition of sebum secretion with phloretin, the skin clears and sebum production drops to a minimum when the glucose blockers are rubbed into the skin.

Phloretin and diallyl stilbersterol are the preferred materials of the invention. Phloretin is the aglucone portion of phlorizin and is a polyphenolic compound. It is split from phlorizin by acid hydrolysis. Alternatively, phloretin can be totally synthesized directly by known procedures. A number of different total synthesis have been described in the literature. Diallyl stillbesterol is similarly a poly phenolic compound as is phloretin.

Surface active compounds which may have additive advantages with respect to skin penetration can be synthesized and added to the lotion.

In addition to phloretin and its derivatives other compositions are also effective in preventing glucose entry into cells and can be used in accordance with the present invention.

Some of these compounds combine with enzymes involved in the transport process while other have a phloridzin-like action and occlude the receptor sites. Cytochalsin B is a complex polyphenolic compound which adheres to the receptor site. A radioactive form of cytochalasin B has been used to determine the number of receptor sites for glucose transport on the cell surface. Like phloridzin, it remains on the surface of the cell. It is very effective and the blockage of glucose entry is nearly complete.

Two Japanese chemists have found that some phenyl-glucosides inhibit uptake of d-glucose by monkey kidney cells. (J.Biochem 88:1399 1980). Lipid soluble derivatives of p-(sec-butyl)phenyl-6-chloro-6-deoxy-B-D-glucopyranoside could provide inexpensive substances could prevent glucose uptake by sebaceous cells.

Some non-metabolizable glucose analogues prevent glucose entry into the cell as well. They do this by competition for the receptor sites on the enzymes. While this attachment to the enzymes is usually temporary, in some cases it is irreversible. D-Xylose is an effective blocker of hexokinase and prevents glucose entry into the cell. (Febs Letter 98:88 1979). Other modifications of glucose also render it non metabolizable and effectively compete with glucose for the receptor site on enzymes. 2-deoxy-d-glucose is such a compound which effectively inhibits hexokinase and prevents entry of glucose cells (Cancer Res. 18:518 1958). The problem with these substances is that they are too polar to penetrate deeply into the skin.

Other analogues of glucose which act similarly are fluroglucose and glucosamine. Fluroglucose (2-deoxy-2-fluro-D-glucose) and glucosamine both inhibit intracellular enzyme systems and interfere with glucose metabolism within the cell. (Eur. J. Biochem. 121:469 1982).

Other compounds unrelated to glucose also inhibit enzyme systems relating to glucose entry into the cell. Oxamic acid, which is a relatively toxic substance. has been shown to inhibit glucose entry into the cell in vitro and suppresses glucose utilization and lactic acid formation. It also prevents cellular multiplication as the result of non availability of glucose. (Jour. Biol. Chem. 236:278 1961). Esters of oxamic acid might be satisfactory for topical application.

Some diphenolic compounds have an even greater inhibitory action then phloretin at lower concentrations. Of special interest in this respect are stilbesterol compounds which are diphenolic compounds. The most familiar of these compounds is diethyl stilbesterol with a structural formula as follows:

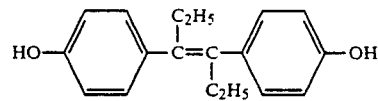

Stilbesterol blocks glucose receptors in the cells as well as does phloretin. Dodds & Lawson (Proc.Roy.-Soc.ser.B 1938, 125:222) have described a number of diphenolics compounds which have estrogenic activity. Many of these compounds have been tested by LeFerve for their ability to block glucose receptors. On a molecular basis 3,3'-Diallyl stilbesterol and 3,3'-Di(2chloroallyl) stilbesterol are the most potent.

These compounds have the added advantage that they are mildly estogenic which also favorably influences acne and makes them quite suitable for females.

The following example demonstrates the method of the present invention:

EXAMPLE

The sebum inhibitor phloretin is dissolved in aqueous propylene glycol solution (Propylene glycol 55%, ethanol 10%, Polyethylene glycol (200) 25%) so that the final concentration of phloretin is about 1 or 2%. Because pure propylene glycol is irritative to the skin its concentration is reduced by the addition of a liquid polyethylene glycol such as is manufactured by Union Carbide under the trade name carbowax 200. The skin is cleansed of oil with cotton soaked in 50-50 alcohol-acetone mixture. A few drops of propylene glycol-phloretin mixture is put on the defatted skin and rubbed into the involved skin area with the fingers. Any excess fluid after a three to five minute rubbing is removed with a cellulose wipe. Phloretin can also be suspended in 50% ethanol containing a non ionic detergent, polyethylene glycol 48% and 2% polyethylene oxide esters of fatty acids as emulsifying agents. The sebum inhibitor should be applied twice a day by inunction. A reduction of sebum secretion is evident a few days after application of the medication.

The reduction in sebum secretion can easily be measured since 90-95% of skin lipids originate from the sebaceous glands. Cigarette paper is affixed to the forehead with adhesive tape. After 3-4 hours, the cigarette paper is removed and weighed. It is then extracted with acetone and reweighed. The loss of weight is the amount of sebum secreted. This test as done in 10 normal males showed a 90-94% reduction in sebum secretion.

While the general embodiments of the present invention have been described, it will be apparent to those of ordinary skill in the art that various alternative configurations and embodiments can readily be adapted to the present invention and are considered to fall within the scope thereof set forth in the following claims.

What is claimed:

1. A method of treating acne located on the sebaceous cells of skin of a human subject by administering topically to the skin a preparation containing a substance selected from the group consisting of stevioside, isoteviol and steviol which blocks glucose entry into said sebaceous cells thereby inhibiting production of sebum.

2. The method of claim 1 wherein said substance is administered at a rate of at least two applications per day.

3. The method of claim 1 wherein said preparation contains a carrier which is propylene glycol or glycerol.

4. A method for treating acne, seborrhea, and oily skin which comprises topically administering to a human subject in need of such treatment in an amount effective to prevent entry of glucose into sebaceous cells thereof and to inhibit production of sebum, a substance selected from the group consisting of 3,3'-Diallyl stilbesterol, 3,3'-Di(2-methylallyl) stilbesterol and 3,3'-Di(chloroallyl) stilbesterol.

5. A method for treating acne, seborrhea, and oily skin which comprises topically administering to a human subject in need of such treatment, phloretin in an amount effective to prevent entry of glucose into sebaceous cells thereof and to inhibit production of sebum.

* * * * *